(12) United States Patent
Sponsel et al.

(10) Patent No.: US 11,065,154 B1
(45) Date of Patent: Jul. 20, 2021

(54) BLEB DRAINAGE DEVICE, OPHTHALMIC PRODUCT AND METHODS

(71) Applicants: William Eric Sponsel, San Antonio, TX (US); A. Mateen Ahmed, Claremont, CA (US)

(72) Inventors: William Eric Sponsel, San Antonio, TX (US); A. Mateen Ahmed, Claremont, CA (US)

( * ) Notice: Subject to any disclaimer, the term of this patent is extended or adjusted under 35 U.S.C. 154(b) by 225 days.

(21) Appl. No.: 15/199,324

(22) Filed: Jun. 30, 2016

Related U.S. Application Data

(62) Division of application No. 13/573,789, filed on Oct. 4, 2012, now Pat. No. 9,381,112.

(60) Provisional application No. 61/544,239, filed on Oct. 6, 2011.

(51) Int. Cl.
*A61F 9/007* (2006.01)

(52) U.S. Cl.
CPC .. *A61F 9/00781* (2013.01); *A61F 2220/0008* (2013.01)

(58) Field of Classification Search
CPC ............... A61F 9/0017; A61F 9/00781; A61F 2220/0008; A61F 2230/001; A61F 2250/0013; A61F 2250/0039
See application file for complete search history.

(56) References Cited

U.S. PATENT DOCUMENTS

| | | | |
|---|---|---|---|
| 3,159,161 A * | 12/1964 | Ness | A61F 9/00781 604/175 |
| 3,654,932 A | 4/1972 | Newkirk et al. | |
| 3,827,439 A | 8/1974 | Schulte et al. | |
| 4,362,681 A | 12/1982 | Spector et al. | |
| 4,457,757 A | 7/1984 | Molteno | |
| 4,521,210 A | 6/1985 | Wong | |
| 4,554,918 A | 11/1985 | White | |
| 4,729,761 A | 3/1988 | White | |
| 4,741,730 A | 5/1988 | Dormandy, Jr. et al. | |
| 4,761,158 A | 8/1988 | Schulte et al. | |
| 4,761,232 A | 8/1988 | Bright | |

(Continued)

FOREIGN PATENT DOCUMENTS

EP 18211968.5 12/2018

OTHER PUBLICATIONS

Batlle OR, Sponsel WE, Swann FB, Margo CE, Groth SL, Ayyala RS. Retrobulbar diversion of aqueous humor: laboratory studies. J Glaucoma. Dec. 2014;23(9):624-7. (Year: 2014).*

(Continued)

*Primary Examiner* — Kai H Weng
(74) *Attorney, Agent, or Firm* — John J. Connors; Connors & Assoc.

(57) ABSTRACT

Fluid is drained from a bleb using a device including a tubular member having opposed open ends to enable the fluid to flow from end to end through the tubular member. Inward from one end is a stop element enabling the one end to be inserted in one direction through a wall of the bleb but preventing the inserted end from being pulled in the opposite direction through the bleb wall. The opposed remote end of the tubular member is inserted into the retrobulbar space to enable fluid exiting the tubular member at this remote end to drain into the tissue. Along an exterior of the tubular member is an anchoring element enabling the device to be sutured in position. An ophthalmic product has a bleb drainage feature.

3 Claims, 7 Drawing Sheets

(56) References Cited

U.S. PATENT DOCUMENTS

| | | |
|---|---|---|
| 4,850,955 A | 7/1989 | Newkirk |
| 5,017,408 A | 5/1991 | Kozak |
| 5,024,671 A | 6/1991 | Tu et al. |
| 5,071,408 A | 12/1991 | Ahmed |
| 5,073,344 A | 12/1991 | Smith et al. |
| 5,181,903 A | 1/1993 | Vann et al. |
| 5,314,471 A | 5/1994 | Brauker et al. |
| 5,370,607 A | 12/1994 | Memmen |
| 5,397,300 A | 3/1995 | Baerveldt et al. |
| 5,411,473 A | 5/1995 | Ahmed |
| 5,417,651 A | 5/1995 | Guena et al. |
| 5,432,100 A | 7/1995 | Smith et al. |
| 5,433,701 A | 7/1995 | Rubinstein |
| 5,433,748 A | 7/1995 | Wellisz |
| 5,454,796 A | 10/1995 | Krupin |
| 5,466,258 A | 11/1995 | Rubin |
| 5,466,259 A | 11/1995 | Durette |
| 5,476,445 A | 12/1995 | Baerveldt et al. |
| 5,489,306 A | 2/1996 | Gorski |
| 5,501,232 A | 3/1996 | Ritleng |
| 5,520,631 A | 5/1996 | Nordquist et al. |
| 5,545,226 A | 8/1996 | Wingo et al. |
| 5,558,629 A | 9/1996 | Baerveldt et al. |
| 5,558,630 A | 9/1996 | Fisher |
| 5,573,544 A | 11/1996 | Simon et al. |
| RE35,390 E | 12/1996 | Smith |
| 5,584,152 A | 12/1996 | Baerveldt et al. |
| 5,601,094 A | 2/1997 | Reiss |
| 5,616,118 A | 4/1997 | Ahmed |
| 5,665,114 A | 9/1997 | Weadock et al. |
| 5,681,275 A | 10/1997 | Ahmed |
| 5,713,888 A | 2/1998 | Neuenfeldt et al. |
| 5,713,955 A | 2/1998 | Durette |
| 5,716,660 A | 2/1998 | Weadock et al. |
| 5,722,948 A | 3/1998 | Gross |
| 5,743,274 A | 4/1998 | Peyman |
| 5,743,869 A | 4/1998 | Ahmed |
| 5,752,928 A | 5/1998 | de Roulhac et al. |
| 5,762,840 A | 6/1998 | Tsai |
| 5,785,674 A | 7/1998 | Ahmed |
| 5,800,512 A | 9/1998 | Lentz et al. |
| 5,807,302 A | 9/1998 | Wandel |
| 5,824,046 A | 10/1998 | Smith et al. |
| 5,824,073 A | 10/1998 | Peyman |
| 5,868,697 A | 2/1999 | Richter et al. |
| 5,873,196 A | 2/1999 | Hoffmann et al. |
| 5,876,435 A | 3/1999 | Swords et al. |
| 5,882,327 A | 3/1999 | Jacob |
| 5,882,354 A | 3/1999 | Brauker et al. |
| 5,908,447 A | 6/1999 | Schroeppel et al. |
| 5,922,024 A | 7/1999 | Janzen et al. |
| 5,941,909 A | 8/1999 | Purkait |
| 5,964,804 A | 10/1999 | Brauker et al. |
| 5,972,366 A | 10/1999 | Haynes et al. |
| 5,977,204 A | 11/1999 | Boyan et al. |
| 5,977,431 A | 11/1999 | Knapp et al. |
| 6,007,510 A | 12/1999 | Nigam |
| 6,018,095 A | 1/2000 | Lerch et al. |
| 6,030,588 A | 2/2000 | Smith et al. |
| 6,058,590 A | 5/2000 | Roberts et al. |
| 6,060,640 A | 5/2000 | Pauley et al. |
| 6,063,117 A | 5/2000 | Perry |
| 6,068,478 A | 5/2000 | Grande et al. |
| 6,069,295 A | 5/2000 | Leitao |
| 6,083,264 A | 7/2000 | Wood et al. |
| 6,099,565 A | 8/2000 | Sakura, Jr. |
| 6,110,205 A | 8/2000 | Nies |
| 6,146,686 A | 11/2000 | Leitao |
| 6,181,973 B1 | 1/2001 | Ceron et al. |
| 6,182,668 B1 | 2/2001 | Tweden et al. |
| 6,187,043 B1 | 2/2001 | Ledergerber |
| 6,193,682 B1 | 2/2001 | Ahmed |
| 6,203,573 B1 | 3/2001 | Walter et al. |
| 6,228,111 B1 | 5/2001 | Tormala et al. |
| 6,235,225 B1 | 5/2001 | Okada et al. |
| 6,261,256 B1 | 7/2001 | Ahmed |
| 6,277,150 B1 | 8/2001 | Crauley |
| 6,281,015 B1 | 8/2001 | Mooney et al. |
| 6,290,982 B1 | 9/2001 | Seppala et al. |
| 6,306,169 B1 | 10/2001 | Lee et al. |
| 6,315,796 B1 | 11/2001 | Eaton |
| 6,332,775 B1 | 12/2001 | Cordils |
| 6,344,496 B1 | 2/2002 | Niederauer et al. |
| 6,352,708 B1 | 3/2002 | Duran et al. |
| 6,399,188 B1 | 6/2002 | Smith et al. |
| 6,409,697 B2 | 6/2002 | Eno |
| 6,520,997 B1 | 2/2003 | Pekkarinen |
| 6,521,284 B1 | 2/2003 | Parsons |
| 6,534,197 B2 | 3/2003 | Noda et al. |
| 6,540,780 B1 | 4/2003 | Zilla et al. |
| 6,551,608 B2 | 4/2003 | Yao |
| 6,553,681 B2 | 4/2003 | Ekholm, Jr. et al. |
| 6,554,857 B1 | 4/2003 | Zilla et al. |
| 6,571,130 B1 | 5/2003 | Ljungstrom et al. |
| 6,591,838 B2 | 7/2003 | Durgin |
| 6,592,513 B1 | 7/2003 | Kroll et al. |
| 6,626,823 B1 | 9/2003 | Campbell et al. |
| 6,629,997 B2 | 10/2003 | Mansmann |
| 6,632,503 B1 | 10/2003 | Shikinami et al. |
| 6,673,075 B2 | 1/2004 | Santilli |
| 6,673,108 B2 | 1/2004 | Zilla |
| 6,699,210 B2 | 3/2004 | Williams et al. |
| 6,702,857 B2 | 3/2004 | Brauker |
| 6,709,452 B1 | 3/2004 | Vallmaa |
| 6,710,093 B2 | 3/2004 | Yao et al. |
| 6,783,499 B2 | 8/2004 | Schwartz |
| 6,815,384 B2 | 11/2004 | Ishikawa |
| 6,833,152 B2 | 12/2004 | Roorda |
| 6,840,960 B2 | 1/2005 | Bubb |
| 6,849,214 B2 | 2/2005 | Patil |
| 6,875,166 B2 | 4/2005 | Kroll |
| 6,881,198 B2 | 4/2005 | Brown |
| 6,916,304 B2 | 7/2005 | Eno |
| 6,995,013 B2 | 2/2006 | Connelly |
| RE39,069 E | 4/2006 | Faour |
| 7,025,740 B2 | 4/2006 | Ahmed |
| 7,033,388 B2 | 4/2006 | Zilla |
| 7,047,981 B2 | 5/2006 | Durgin |
| 7,066,962 B2 | 6/2006 | Swords |
| 7,077,821 B2 | 7/2006 | Durgin |
| 7,094,226 B2 | 8/2006 | Yaacobi |
| 7,097,451 B2 | 8/2006 | Tang |
| 7,118,695 B2 | 10/2006 | Lin |
| 7,131,997 B2 | 11/2006 | Bourne |
| 7,147,846 B2 | 12/2006 | Anderson |
| 7,192,450 B2 | 3/2007 | Brauker |
| 7,201,917 B2 | 4/2007 | Malaviya |
| 7,226,615 B2 | 6/2007 | Yuksel |
| 7,244,270 B2 | 7/2007 | Lesh |
| 7,314,636 B2 | 1/2008 | Caseres |
| 7,338,517 B2 | 3/2008 | Yost |
| 7,364,546 B2 | 4/2008 | Sniegowski et al. |
| 7,378,144 B2 | 5/2008 | DeMeo |
| 7,384,550 B2 | 6/2008 | Rodgers et al. |
| 7,390,498 B2 | 6/2008 | Dalal |
| 7,399,312 B2 | 7/2008 | Bicek |
| 7,431,734 B2 | 10/2008 | Danoff |
| 7,458,953 B2 | 12/2008 | Peyman |
| 7,500,988 B1 | 3/2009 | Butaric |
| 7,507,469 B2 | 3/2009 | Mao et al. |
| 7,524,335 B2 | 4/2009 | Slivka |
| 7,534,448 B2 | 5/2009 | Saltzman |
| 7,550,091 B2 | 6/2009 | Beaty |
| 7,588,686 B2 | 9/2009 | Jensen |
| 7,632,228 B2 | 12/2009 | Brauker |
| 7,632,306 B2 | 12/2009 | Zilla |
| 7,648,726 B2 | 1/2010 | Liu |
| 7,655,047 B2 | 2/2010 | Swords |
| 7,674,517 B2 | 3/2010 | Ramsey et al. |
| 7,682,540 B2 | 3/2010 | Boyan |
| 7,699,882 B2 | 4/2010 | Stamper |
| 7,727,274 B2 | 6/2010 | Zilla |
| 7,731,988 B2 | 6/2010 | Thomas |
| 7,789,908 B2 | 9/2010 | Sowinski |

(56) References Cited

U.S. PATENT DOCUMENTS

| | | |
|---|---|---|
| 7,795,346 B2 | 9/2010 | Martin |
| 7,803,178 B2 | 9/2010 | Whirley |
| 7,803,183 B2 | 9/2010 | Kutryk |
| 7,806,922 B2 | 10/2010 | Henderson |
| 7,807,210 B1 | 10/2010 | Roorda |
| 7,811,268 B2 | 10/2010 | Maldon Ado Bas |
| 7,815,826 B2 | 10/2010 | Serdy |
| 7,815,923 B2 | 10/2010 | Johnson |
| 7,833,615 B2 | 11/2010 | Ramsey |
| 7,850,862 B2 | 12/2010 | Amrich |
| 7,854,958 B2 | 12/2010 | Kramer |
| 7,901,462 B2 | 3/2011 | Yang |
| 7,910,124 B2 | 3/2011 | Boyan |
| 7,939,000 B2 | 5/2011 | Edwin |
| 7,943,162 B2 | 5/2011 | Missel |
| 7,998,202 B2 | 8/2011 | Lesh |
| 7,998,523 B2 | 8/2011 | Lerf |
| 8,002,830 B2 | 8/2011 | Boyan |
| 8,007,823 B2 | 8/2011 | Favis |
| 8,025,896 B2 | 9/2011 | Malaviya |
| 8,062,739 B2 | 11/2011 | Liu |
| 8,066,770 B2 | 11/2011 | Rivard |
| 8,066,778 B2 | 11/2011 | Meridew |
| 8,071,124 B2 | 12/2011 | Yuksel |
| 8,118,866 B2 | 2/2012 | Brauker |
| 8,118,867 B2 | 2/2012 | Perry |
| 8,118,877 B2 | 2/2012 | Brauker |
| 8,124,187 B2 | 2/2012 | Su |
| 8,128,689 B2 | 3/2012 | Weber |
| 8,128,706 B2 | 3/2012 | Kalgler |
| 8,632,489 B1 | 1/2014 | Ahmed |
| 2007/0118065 A1* | 5/2007 | Pinchuk ............ A61F 9/00781 604/9 |
| 2010/0010416 A1* | 1/2010 | Juan, Jr. ............ A61F 9/0017 604/9 |

OTHER PUBLICATIONS

Sponsel WE, Groth S, March de Ribot F, Ramos H, Puig M. Efficacy of a Novel Retrobulbar Extension Shunt to Rescue Eyes with Fibrotic Encapsulated Blebs and Uncontrolled Ocular Hypertension. Graefes Arch Clin Exp Ophthalmol. Apr. 2019;257(4):791-798. (Year: 2019).*

Sponsel WE, Groth SL, Ayyala RS. Retrobulbar diversion of aqueous humor: clinical feasibility studies. J Glaucoma. Dec. 2014;23(9):628-32. (Year: 2014).*

U.S. Appl. No. 13/573,789, filed Jul. 25, 2014, Sponsel office action, our 9960s.

Hyun Bong Bae,M.D., A Membranous Drainage Implant in GlaucomaFiltering Surgery: Animal Trial, Kor J. Ophthalmol. vol. 2:49-56, 1988, 8 pages.

NHS Executive, Good Practice, Action On Cataracts, Jan. 2000, 62 pages.

A. Reidy et al. Prevalence of Serlos Eye Disease and Visual Impairment in a North London Population: Population Based, Cross Section Study, BMJ vol. 316, May 30, 1998, 4 pages.

D.C. Minassian et al, The Deficit in Cataract Surgery in England and Wales and the Escalating Problem of Visual Impairment . . Br. J. Opthalmol 2000 84:4-8, 6 pages.

A M S Morley et al, The Future of Glaucoma Clinics, Br.J Ophthalmol. 2006;90:640-645, 6 pages.

* cited by examiner

BLEB DRAINAGE DEVICE, OPHTHALMIC PRODUCT AND METHODS

INCORPORATION BY REFERENCE

This divisional application claims the benefit under 35 U.S.C. 120 U.S. Utility patent application Ser. No. 13/573,789, entitled "Bleb Drainage Device, Ophthalmological Product and Methods," filed Oct. 4, 2012, which claims the benefit under 35 USC 119(e) of U.S. Provisional Patent Application No. 61/544,239, entitled "Bleb Drainage Device and method," filed Oct. 6, 2011. This related application is incorporated herein by reference and made a part of this application. If any conflict arises between the disclosure of the invention in this utility application and that in the related provisional application, the disclosure in this utility application shall govern. Moreover, any and all U. S. patents, U. S. patent applications, and other documents, hard copy or electronic, cited or referred to in this application are incorporated herein by reference and made a part of this application.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The words "substantially" and "essentially" have equivalent meanings.

The word "bleb" may be one organically formed from a patient's tissue or be one comprising an artificial enclosure surgically implanted in a patient.

BACKGROUND

Fibrous scar tissue, commonly referred to as an encapsulated bleb (herein bleb), may encase an implanted medical device and can interfere with the proper functioning of such devices. This problem has been encountered with the Ahmed® glaucoma valve sold by New World Medical, Inc. of Rancho Cucamonga, Calif., and described in U.S. Pat. No. 5,071,408. We have invented a bleb drainage device, an ophthalmic product, and methods which can be used to overcome this problem in the Ahmed® glaucoma valve and other implantable medical devices encountering similar problems by draining fluid to the retrobulbar space. This area of the eye is largely comprised of periorbital fat that is hydrophobic and has limited blood supply, potentially resulting in a reduced foreign body response when aqueous is shunted to it.

SUMMARY

Our bleb drainage device, ophthalmic product, and methods have one or more of the features depicted in the embodiments discussed in the section entitled "DETAILED DESCRIPTION OF SOME ILLUSTRATIVE EMBODIMENTS." The claims that follow define our bleb drainage device, ophthalmic product, methods, distinguishing them from the prior art; however, without limiting the scope of our bleb drainage device, ophthalmic product, methods as expressed by these claims, in general terms, some, but not necessarily all, of their features are:

One, our bleb drainage device includes a tubular member having opposed open ends enabling fluid to flow from end to end through the tubular member. Inward from one end is a stop element enabling the one end to be inserted in one direction through one portion of a wall of a bleb but preventing the one inserted end from being pulled in the opposite direction through the bleb wall. A hermetic seal is created upon inserting the tubular member into the bleb at the point of insertion. Along an exterior of the tubular member is at least one anchoring element that enables the device to be sutured in position, for example, a pair of suturing sites may be used that straddle a central reference line of the tubular member and are opposed to each other. The opposed open ends of the tubular member may be beveled. The stop element may be a flexible member that bends as it passes through a surgical incision in the bleb wall and then returns to an unbent condition after passing through the surgical incision. The stop element may have a substantially truncated conical configuration that tapers towards the one inserted end. The bleb drainage device may be molded from a biocompatible material. It also may be made of a metal.

Two, the distance from the one inserted end to the stop member is, for example, less than the distance between the one portion of the bleb wall where the one inserted end enters the bleb and another portion of the bleb wall opposite the one portion of the bleb wall. This distance from the one inserted end to the stop member is, for example, less than 14 millimeters. The tubular member may have a length substantially from 5 to 60 millimeters, an outside diameter substantially from 0.2 to 3 millimeters, an inside diameter substantially from 0.1 to 3 millimeters. The stop element may be inward from the one inserted end substantially from 1 to 14 millimeters, and the distance between the stop element and the other opposed end of the tubular member may be substantially from 3 to 45 millimeters.

Three, the tubular member may be substantially straight to facilitate inserting the one end into a posterior portion of the bleb, or it may be bent to facilitating inserting the one end into an anterior portion of the bleb. A flexible tubular member can be bent substantially at an angle from 0 to 170 degrees. For example, the bleb drainage device may include a bending component comprising a tubular guide element configured to enable the tubular member to pass therethrough prior to insertion into the bleb a portion of the tubular member. The tubular member is bent near the stop element and between the stop element and the other opposed open end of the tubular member. For example, the distance between the bent part of the tubular member and the other opposed open end of the tubular member is substantially from 5 to 40 millimeters. The tubular member may comprise a pair of legs connected by an accordion-type wall that allows the legs to be moved relative to each other.

Four, the bleb drainage device may have in a wall forming the tubular member openings therein that are substantially orthogonal to the inserted end of the tubular member. These openings may be at or near one or both opposed ends of the tubular member. The stop element may be tapered, and it may have a maximum diameter of 10 millimeters. The anchoring element may be offset with respect to a longitudinal reference line extending along the tubular member, and the anchoring element may be oriented to intersect a longitudinal reference line extending along the tubular member with the tubular member projecting through the anchoring element.

One embodiment of our ophthalmic product uses an artificial bleb. It includes a glaucoma drainage device having a tube extending from the glaucoma drainage device. The tube has a terminal end adapted to be inserted into an intraocular chamber of a patient's eye. A membrane forms an enclosure that at least partially encloses the glaucoma drainage device. A tubular member passes through a wall of the enclosure. The tubular member has a first portion within the enclosure and a first end terminating within the enclosure and a second portion projecting from the enclosure and having a second end. The second portion has a predetermined length so that, upon implantation of the ophthalmic device, the second end is adapted to be placed in or near the retrobulbar space of an eye of a patient.

The enclosure functions as an artificial bleb to collect fluid draining from the intraocular chamber through the tube into the enclosure, and the fluid in the enclosure drains through the tubular member into the retrobulbar space. The glaucoma drainage device may include a plate and the membrane is affixed to the plate to form a sealed enclosure that only allows fluid to be drained from the enclosure through the tubular member. The membrane may be elastic and comprises biocompatible silicone plastic. The glaucoma drainage device may include a self-actuating glaucoma valve mounted on a plate. The valve is within the enclosure and opens and closes in response to intraocular pressure to drain fluid from the intraocular chamber into the enclosure. The second portion may have an anchoring element.

Broadly, our method of draining fluid from a bleb, artificial or organic, encasing a glaucoma drainage device comprises draining fluid within the bleb through a tubular member passing through a wall of the bleb and terminating in or near the retrobulbar space of an eye of a patient. One embodiment of our method includes the steps of (a) providing a bleb drainage device comprising
a tubular member having opposed open ends enabling fluid to flow from end to end through the tubular member, inward from one end a stop element enabling the one end to be inserted in one direction through a wall of a bleb but preventing the inserted end from being pulled in the opposite direction through the bleb wall, and along an exterior of the tubular member at least one anchoring element, (b) inserting the one end through a wall of the bleb, pushing in one direction until the stop element and the inserted end are completely within the interior of the bleb, (c) inserting the other opposed end of the tubular member into a retrobulbar space to enable fluid exiting the tubular member at this other opposed end to drain into said space, (d) suturing the device in position by the anchoring element.

We also invented a method of treating glaucoma. This method comprises (a) implanting in a patient's eye a glaucoma drainage device within an enclosure and having a tube extending from the glaucoma drainage device having a terminal end and a tubular member passing through a wall of the enclosure and having a first portion within the enclosure and a first end terminating within the enclosure and a second portion projecting from the enclosure and having a second end, (b) inserting the terminal end of the tube into an intraocular chamber of the eye of the patient to drain fluid from the intraocular chamber, said enclosure functioning as an artificial bleb to collect fluid draining from the intraocular chamber through the tube into the enclosure, and (c) placing the second end of the tubular member in or near retrobulbar space of the eye of the patient, with fluid in the enclosure draining through the tubular member into the retrobulbar space.

These features are not listed in any rank order nor is this list intended to be exhaustive.

DESCRIPTION OF THE DRAWING

Some embodiments of our bleb drainage device, ophthalmic product, and methods, are discussed in detail in connection with the accompanying drawing, which is for illustrative purposes only. This drawing includes the following figures (Figs.), with like numerals indicating like parts.

Figure 1:
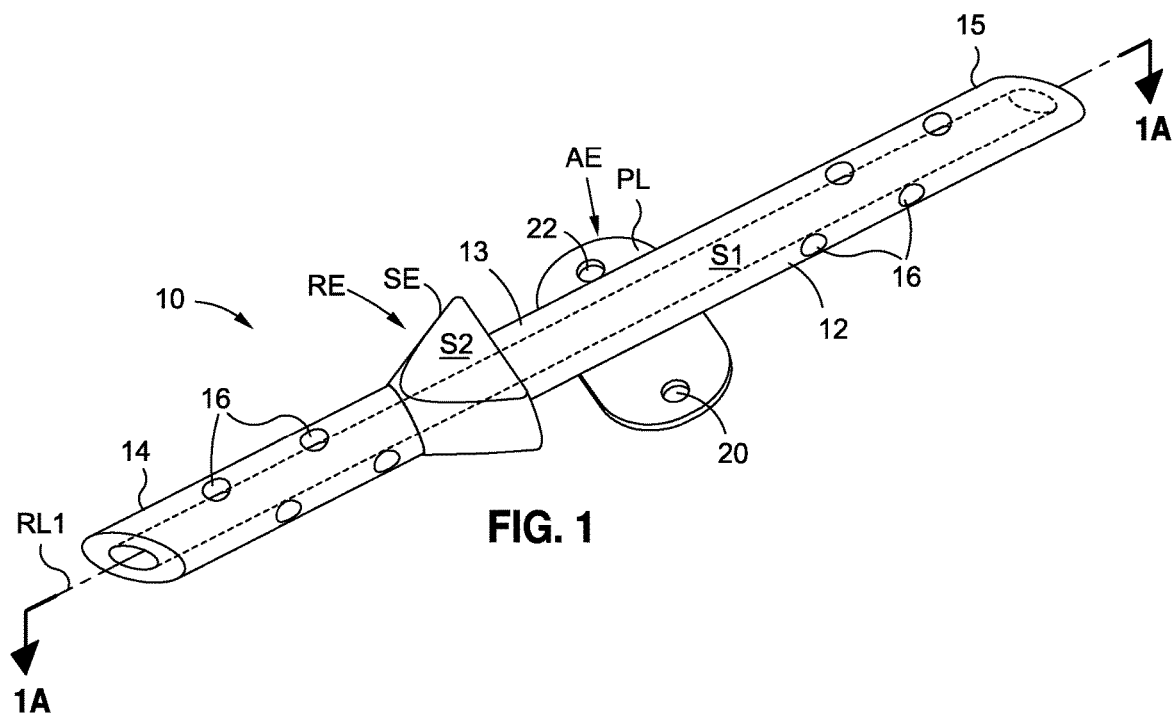
FIG. 1 is a perspective view of one embodiment of our bleb drainage device.
Figure 1A:
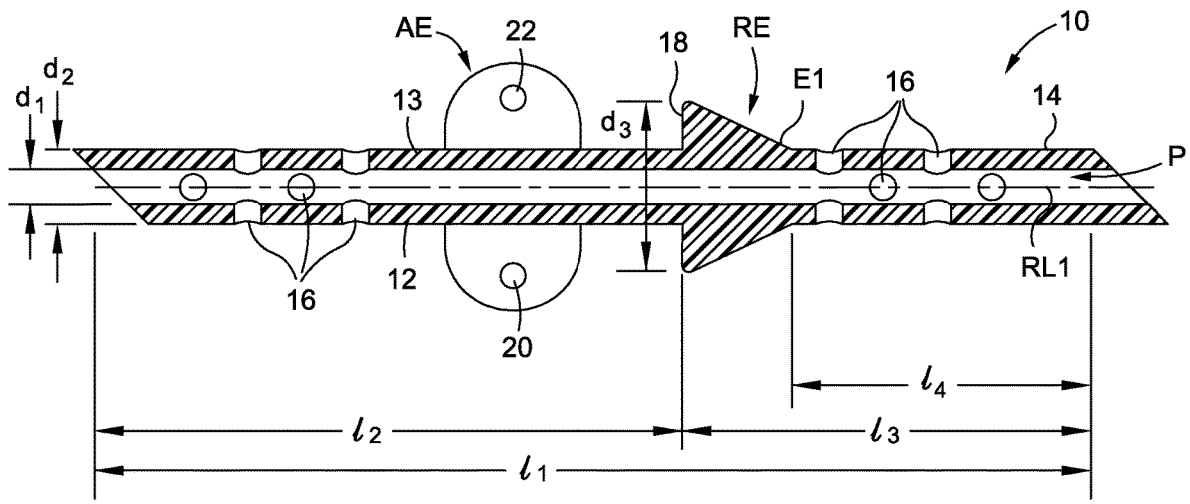
FIG. 1A is a cross-sectional view taken along line 1A-1A of FIG. 1.

Photos Stills Numbered 1 through 16 are photographs of our method being practiced where the device shown in FIGS. 1 and 1A is inserted into a posterior portion of a bleb.

Photos Stills Numbered 17 and 18 are ultrasound biomicroscopic images of our bleb drainage device implanted into a bleb.

DETAILED DESCRIPTION OF SOME ILLUSTRATIVE EMBODIMENTS

Bleb Drainage Device

Figure 6:
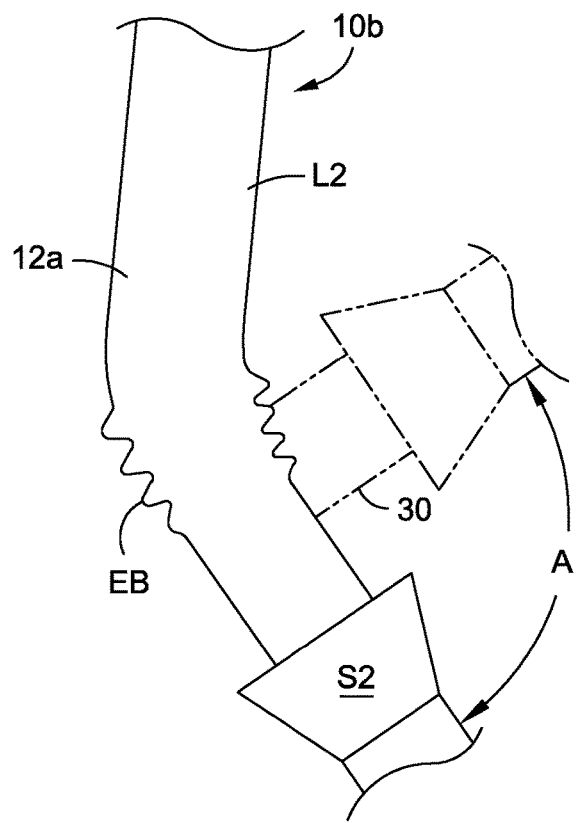
FIG. 6 is a fragmentary view of another embodiment of our bleb drainage device employing a flexible connecting elbow.

There are a number of embodiments of our bleb drainage device illustrated: One embodiment in FIGS. 1 and 1A generally designated by the numeral 10, another embodiment in FIG. 1C generally designated by the numeral 10', another embodiment in FIG. 1D generally designated by the numeral 10", another embodiment in FIG. 2 generally designated by the numeral 10a, another embodiment in FIG. 2A generally designated by the numeral 10a', a sixth embodiment in FIG. 6 is generally designated by the numeral 10b, and a seventh embodiment generally in FIGS. 7 and 7A generally designated by the numeral 10c. Each embodiment includes a tubular member that may have a circular cross-section, but other shapes may be employed. In the devices 10, 10' and 10" the tubular member is generally designated by the numeral 12, and in the devices 10a, 10a', and 10b the tubular member is generally designated by the numeral 12a. In the device 10c the tubular member is generally designated by the numeral 12c. The tubular members 12, 12a and 12c have opposing open ends 14 and 15 and 14a and 15a, respectively, which may be beveled.

Figure 3:
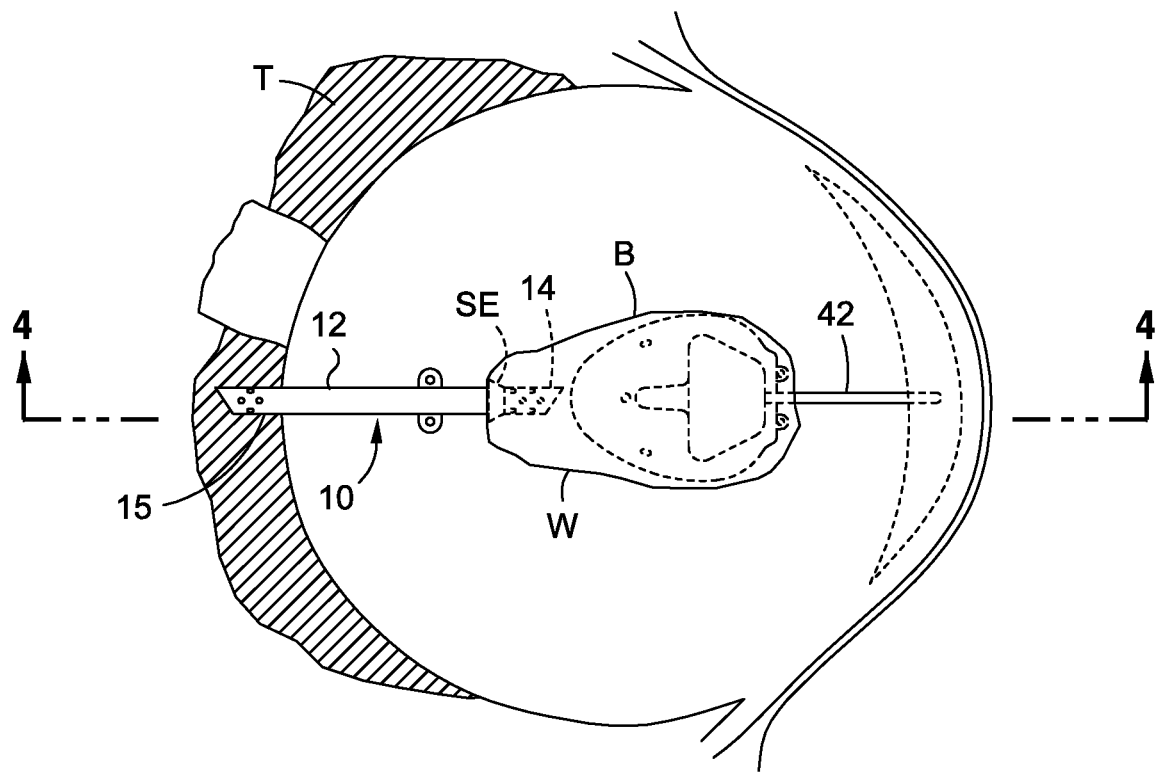
FIG. 3 is a schematic diagram depicting the embodiment shown in FIG. 1 having one end inserted into a posterior portion of a bleb encasing a glaucoma self-regulating valve and its opposed end inserted into the retrobulbar space.
Figure 4:
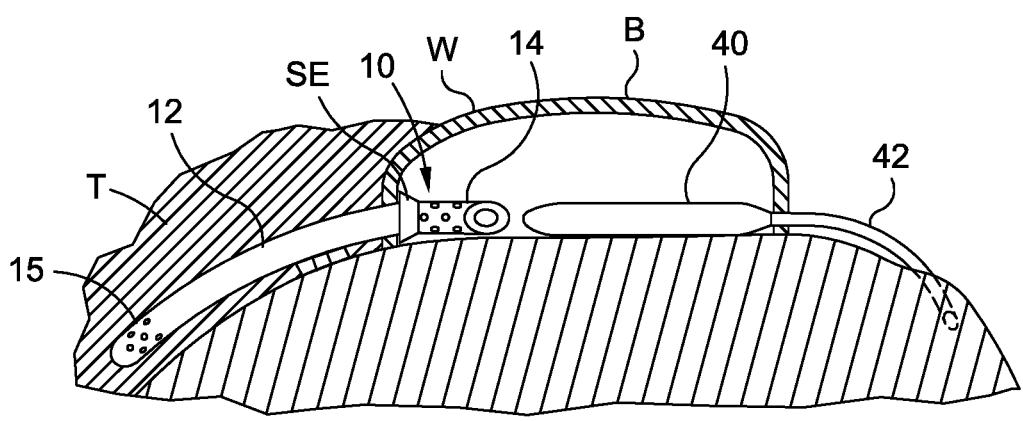
FIG. 4 is a cross-sectional view taken along line 4-4 of FIG. 3.

All the aforementioned embodiments are designed to drain a non-percolating bleb, that is, a bleb having a wall that is substantially non-porous to prevent fluid from passing through it. When such a non-percolating bleb encases an Ahmed® glaucoma valve, it prevents the outflow of aqueous from the valve, leading to pressure increase within the eye. In the bleb drainage devices 10 and 10' its tubular member 12 is substantially straight to facilitate inserting its forward or proximal end 14 into a posterior portion of a non-percolating bleb B (FIGS. 3 and 4). In the bleb drainage device 10a its tubular member 12a is bent to facilitate inserting its forward or proximal end 14a (FIG. 5) into an anterior portion of the bleb. The tubular members 12, 12a and 12c each have a wall 13 (FIG. 1A) forming a passageway P that extends along a longitudinal central reference line RL1 between the opposed open ends 14, 15 and 14a, 15a of the tubular members, enabling fluid to flow from end to end along the passageway through a tubular member. Portions of the wall 13 at or near the opposed ends 14, 15 and 14a, 15a of the tubular members 12 and 12a have openings 16 therein. These openings 16 may be circular perforations or of other configurations that assist in enabling fluid to enter and exit the opposed open ends of the tubular members. If the open ends of the tubular members become blocked by debris, the openings 16 allow fluid to still enter and exit the tubular members.

Figure 1B:
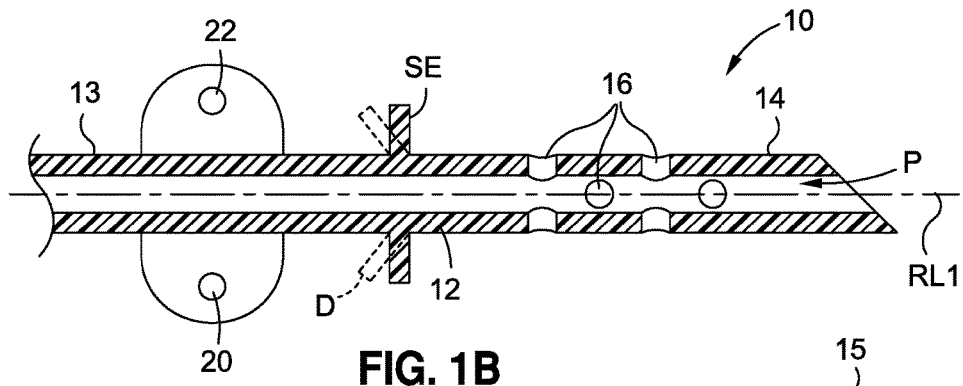
FIG. 1B is a fragmentary cross-sectional view of an embodiment of our device using a flexible diaphragm as a stop element.

Inward from the one end that is to be inserted into the bleb B (the end 14 in the devices 10 and 10' and the end 14a in the devices 10a, 10b and 10c) is a stop element SE. This stop element SE is configured to prevent our bleb drainage device from being pulled from the bleb wall W (FIG. 4) after being pushed into the interior of the bleb B through a surgical incision in the bleb wall. The size of the stop element SE is such that it does not tear the bleb wall when it is inserted through the surgical incision. Once inserted, the stop element SE also prevents peritubular leakage by way of a hermetic seal at the interface between bleb tissue and the stop element. In the embodiments depicted, the stop element SE may be a ramp element RE (FIG. 1A) or a flexible, thin wall diaphragm or flap D (FIG. 1B). The ramp element RE is tapered, slanting downward from a flat, annular, rear wall 18 (FIG. 2) that intersects at a substantially right angle with the exterior surface S1 (FIG. 1) of the wall 13 to provide a conical-like surface S2 that has an edge E1 terminating near the one end that is to be inserted into the bleb B (the end 14 in the devices 10 and 10' and the end 14a in the devices 10a, 10b and 10c). In other words, the stop element SE has a substantially truncated conical-like configuration. In the embodiment shown in FIG. 1B, the flexible flap D is annular and bends to move into the position shown in dotted lines in FIG. 1B to present a conical surface as the flap passes through a surgical incision in the bleb wall W. And then, because it is resilient, returns to an unbent condition shown in solid lines in FIG. 1B after passing through the surgical incision into the interior of the bleb B. In both embodiments the maximum diameter d of the stop element SE is 10 millimeters. Other embodiments may utilize different shapes including collapsible elements that allow for easy insertion.

Figure 1C:
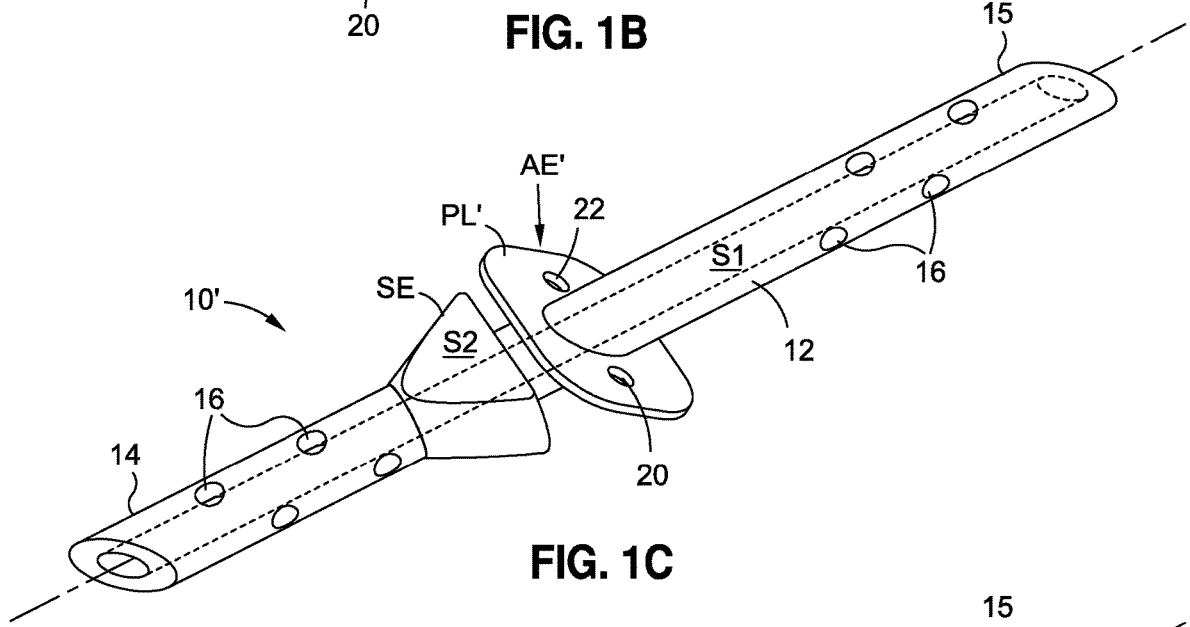
FIG. 1C is a perspective view of another embodiment of our bleb drainage device similar to that shown in FIG. 1 except its anchoring element is oriented for attachment to a bleb wall.
Figure 1D:
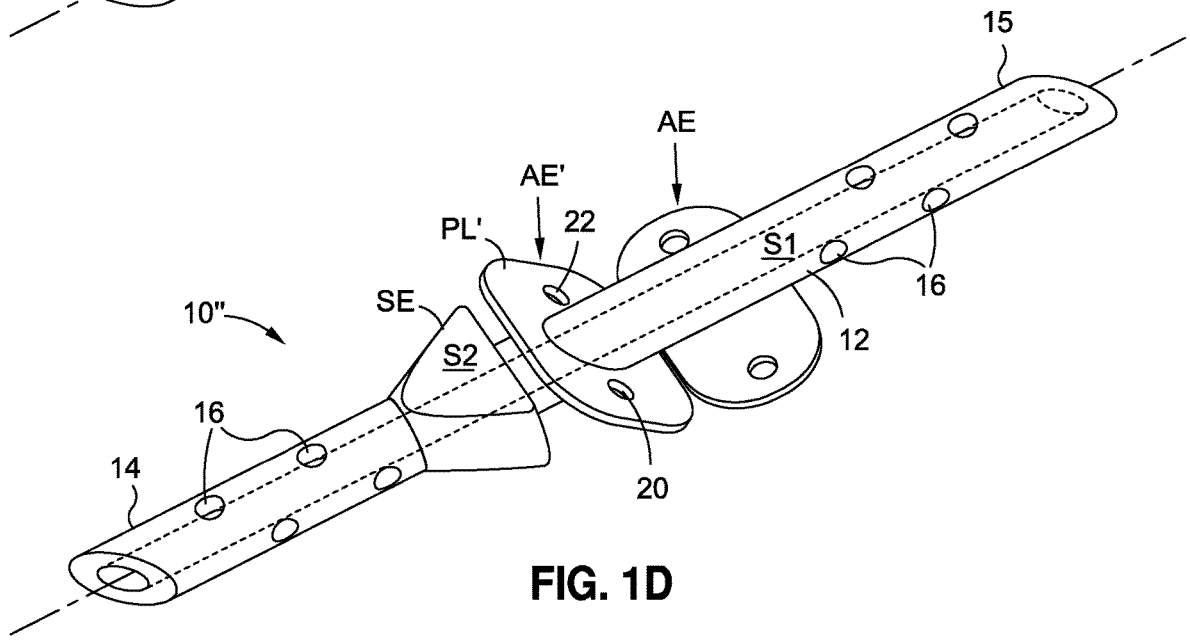
FIG. 1D is a perspective view of another embodiment of our bleb drainage device depicting a two-component anchoring element.

In each embodiment, along exterior surfaces S1 of each of the tubular members 12 and 12a is an anchoring element AE that enables our bleb drainage device to be sutured in position. The anchoring element AE may be oriented differently. For example, in FIG. 1, the anchoring element AE is oriented to be sutured to the sclera nearby the bleb. In FIG. 1C, the anchoring element AE is oriented to be sutured to the bleb. The anchoring element AE may include a pair of opposed suturing sites that may straddle the central reference line RL1 of a tubular member. In the embodiments depicted, a plate functions as the anchoring element AE. As shown in FIG. 1, a plate PL is attached to the underside of the tubular member 12 and is offset with respect to the longitudinal central reference line RL1. As shown in FIG. 1C, a plate PL' intersects the longitudinal central reference line RL1 and projects through the tubular member 12. The anchoring element AE may be between the stop element SE and the other opposed open remote or distal ends 15 or 15a, as the case may be, of the tubular members 12 and 12a, respectively. In the embodiments depicted, the anchoring element AE comprises a plate PL having spaced apart openings 20 and 22 that straddle the reference line RL1 and are opposed to each other. In embodiment using the tubular member 12a the anchoring element AE is at the bend.

Figure 5:
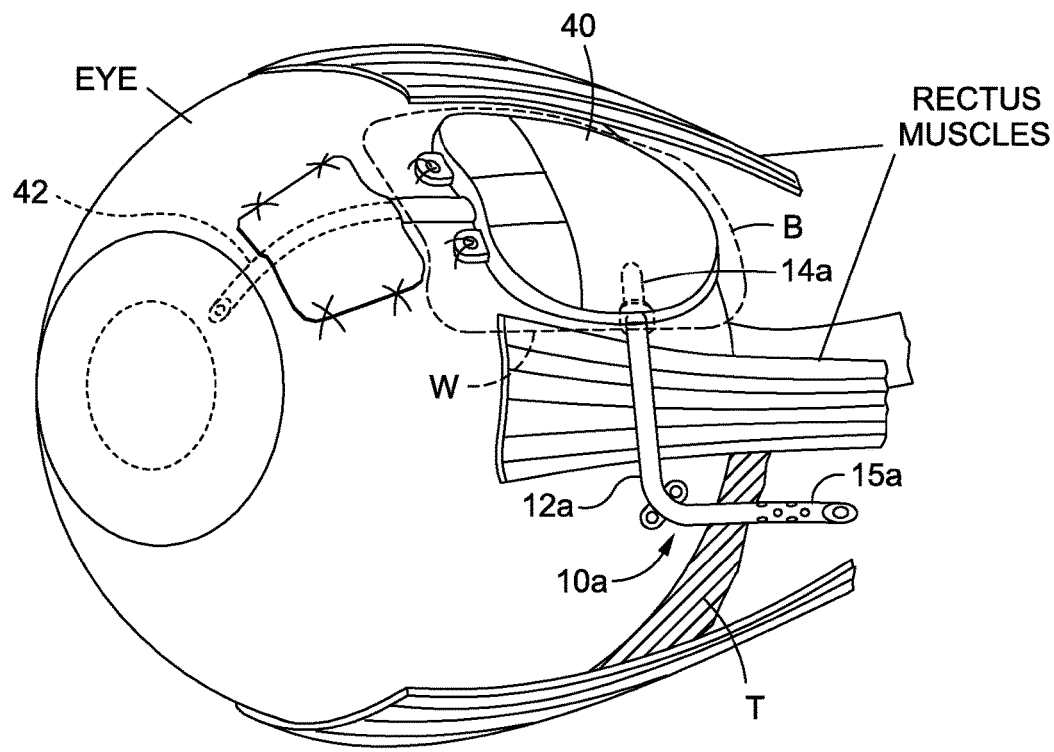
FIG. 5 is a schematic diagram depicting the embodiment shown in FIG. 2 having one end inserted into an anterior portion of a bleb encasing a glaucoma self-regulating valve and its opposed end inserted into the retrobulbar space.

In our bleb drainage device, the tubular member may be flexible or rigid depending on its use. In general, it may be used to drain fluid from any bleb that encases a medical device 40 (FIG. 4). Consequently, it may be made of many different biocompatible materials, including plastics and metals. For example, the biocompatible materials may be polyethylene, polypropylene, silicone, a fluorocarbon polymer such as, for example, Teflon®, PMMA, PHEMA, stainless steel or titanium. For example, when used to drain a bleb encasing an implanted medical valve, our device is made of silicone elastomer, which is a soft, flexible, and resilient material that is injection or compression molded to make a suitable device for this application. Additionally, the biocompatible material may be porous to allow for better integration into the surrounding tissue with pore size between 5 and 40 microns (μm). Size is important to enable our bleb drainage device to be implanted in an eye of a patient as depicted in FIGS. 3 through 5. In the device 10 the straight tubular member 12 has an overall length $l_1$ substantially from 5 to 60 millimeters, a length $l_2$ between the end 15 and the wall 18 substantially from 3 to 45 millimeters, a length $l_3$ between the wall 18 and the end 14 substantially from 1 to 15 millimeters, a length $l_4$ between the edge E1 and the end 14 substantially from 1 to 14 millimeters, and an inside diameter $d_1$ substantially from 0.1 to 3 millimeters and an outside diameter $d_2$ substantially from 0.2 to 3 millimeters. The annular wall 18 has a diameter $d_3$ substantially from 1 to 10 millimeters.

The dimensions of the tubular members 12 and 12a in the forward sections of the devices 10 and 10a are substantially identical. In the device 10a, the tubular member 12a is bent near the stop element SE and between the stop element and its open end 15a to form an L-shaped member LM including the legs L1 and L2. The L-shaped member LM enables the end 14a to access the anterior portion of the bleb B upon inserting the device into the bleb. The main difference between the tubular members 12 and 12a is that the one leg L2 is longer than the overall length of the device 10. The tubular member 12a has its one leg L1 extending between a central longitudinal reference line RL2 of the other leg L2 and the end 14a a distance or length $l_5$ that is substantially from 5 to 30 millimeters. The distance or length $l_6$ between the reference line RL2 and the wall 18 of the anchoring element AE is substantially from 2 to 20 millimeters. The other leg L2 extends between a central longitudinal reference line RL3 and the end 15a and is substantially from 5 to 40 millimeters. In both embodiments the stop element SE is inward from the one end 14 or 14a, as the case may be, substantially the same distance, or the length $l_4$ of substantially from 1 to 14 millimeters. The legs L1 and L2 form an angle A that is substantially from 0 to 180 degrees.

The device 10a has the legs L1 and L2 joined in a manner that inhibits relative movement between these legs. As illustrated in FIG. 6, in the device 10b the legs L1 and L2 are joined by a flexible connecting elbow EB comprising an accordion-type wall 30 that is twisted to allow the legs L1 and L2 to be moved relative to each other. In other words, the angle A may be changed as desired by the surgeon upon inserting this embodiment of our device, allowing the elbow angle to be manually manipulated into a wide variety of different angles falling between the position shown in solid lines in FIG. 6 and the position shown in dotted lines in FIG. 6.

Figure 7:
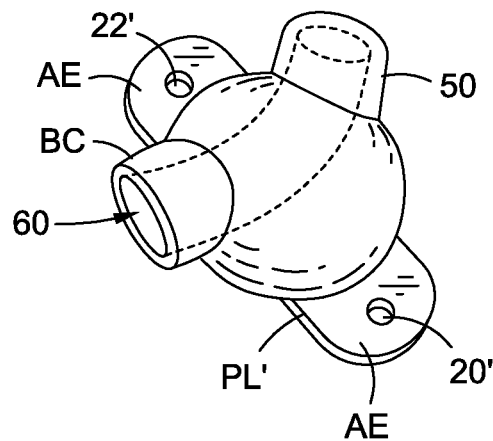
FIG. 7 is a perspective view of a bending component that may be used to bend an embodiment of our bleb drainage device without an anchoring element; the bending component includes an anchoring element.
Figure 7A:
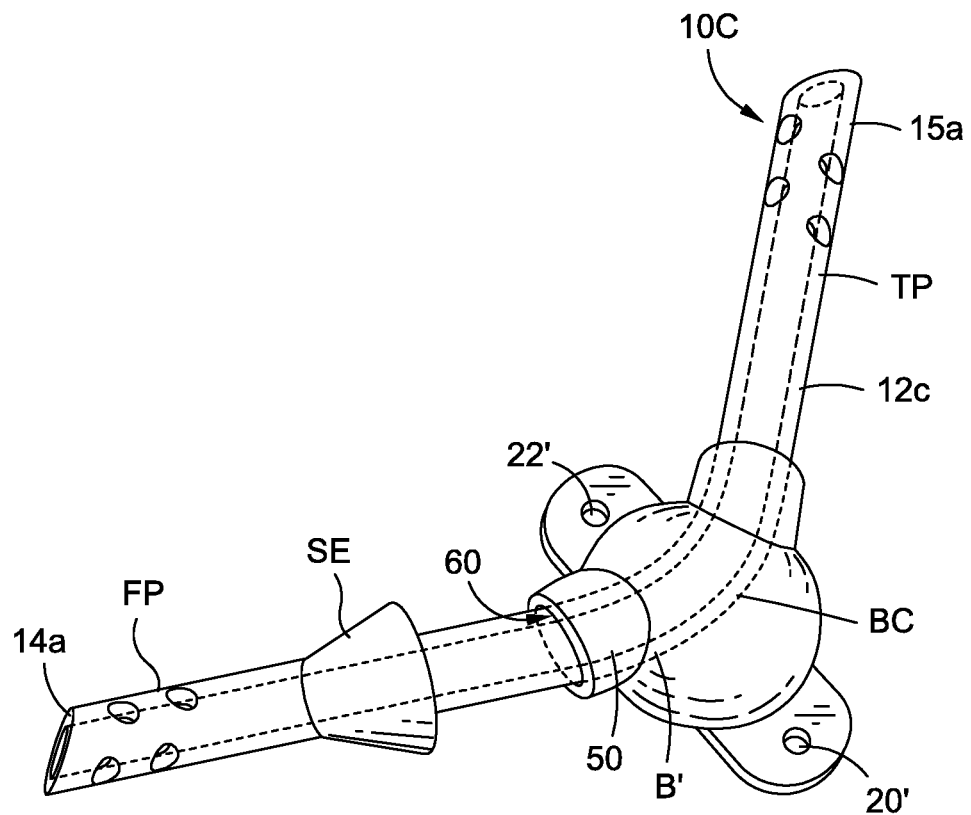
FIG. 7A is a perspective view showing the combination of bleb drainage device without an anchoring element held by the bending component.

The embodiment shown in FIGS. 7 and 7A illustrates our bleb drainage device 10c. It includes a bending component BC (FIG. 7) and a flexible tubular member 12c. The bending component BC is a sleeve member that functions as a tubular guide element 50 configured as shown in FIG. 7A to enable a trailing portion TP of the flexible tubular member 12c to pass therethrough prior to insertion of a forward portion FP of the tubular member 12c into the bleb. In the embodiment depicted, the tubular guide element 50 has a passageway 60 that is bent at an angle substantially of 90 degrees. The bend, however, may range from 0 to 180 degrees. At the bend B' are located, along an exterior of the tubular guide element 50, at least one anchoring element AE that enables the tubular guide element to be sutured in position, for example, a plate PL' having spaced apart openings 20' and 22'. The surgeon inserts into the passageway the tailing portion TP of the flexible tubular member 12c, which bends as its end 15a moves through the bending component BC. The surgeon may adjust the lengths of the portions of the tubular member 12c projecting from each side of the bending component BC. The length of the tailing portion TP may also be adjusted by cutting off any excess or unwanted portion projecting through the bending component BC. This allows the surgeon to determine the exact length of tubing needed or desired on each side of the bending component BC.

Other embodiments include a curved tube to allow placement into the lateral or medial bleb wall, or a j-tube for anterior insertion as shown in 2A. Additional suturing grommets are also available on other embodiments for suturing a posterior portion of the tubular member to the sclera or bleb wall.

Bleb Drainage Method

In accordance with our method as shown in FIGS. 3 through 5, the leading proximal end nearby the stop element SE, the forward end 14 or 14a as the case may be, is inserted through an incision in the wall W of the bleb B, pushing in one direction until the stop element SE is completely within the interior of the bleb B. A rear section of the tubular members 12 and 12a extends from the bleb B, enabling a remote or distal end, ends 15 or 15a as the case may be, to be inserted into the retrobulbar space T. Thus fluid exiting a remote or distal end 15 or 15a drains into the retrobulbar space T. Sutures are tied to the anchoring element AE to hold our drainage device in position.

As depicted in FIG. 5., when the medical device 40 is the self-regulating Ahmed® glaucoma valve implanted on the surface of the globe of an eye, a tube 42 extends from the valve into the intraocular chamber of the eye. Fluid in this chamber flows through the valve 40 when the valve opens. The valve 40 opens and closes in response to a differential in pressure across a valve outlet that is a slit opening (not shown) created by a folded membrane. When the intraocular pressure within the anterior chamber of the eye is about 10-15 millimeters of mercury (mm Hg), this is normally greater than the external pressure around the implanted Ahmed® glaucoma valve, so the valve opens. When this external pressure is greater than about 10-15 mm Hg, the valve is shut closed. Over the course of a few months in some patients a bleb B may slowly form that encases the Ahmed® glaucoma valve, with the tube 42 passing through the wall W of the bleb. When the bleb wall W is only partially formed or very thin, fluid exiting the valve outlet passes through this bleb wall. But as the bleb wall W becomes thicker and impenetrable, fluid collects within the interior of the bleb B so the pressure differential across the valve outlet is such that it prevents the proper functioning of the Ahmed® glaucoma valve. One way to overcome this problem is to drain fluid from the bleb B to relieve the excess pressure within the bleb, restoring the Ahmed® glaucoma valve to its proper functioning.

The ultrasound biomicroscopic images shown in Still 17.JPG and Still 18.JPG d how our bleb drainage device is implanted into a bleb. Our device is surrounded by fluid. The tissue above the implanted device is the thick, fibrous wall of the bleb. Unlike blebs found in other glaucoma filtering procedures such as trabeculectomy, a bleb around a drainage device such as the Ahmed® glaucoma valve is mainly filled with fluid.

According to one embodiment of our method, the proximal end 14 of our device 10 shown in FIG. 1 is inserted into a posterior portion of a bleb B to relieve pressure. Still Photos 1-16 illustrate the main steps of this procedure:

Step 1: The device is removed from its sterile packaging (Still 1.jpeg). The illustrated version of our device has a stop element and an anchoring element. Its tube is perforated at its two ends. This straight version is appropriate for posterior bleb placement, and the following description applies to that approach.

Step 2: A stay suture is placed through the conjunctiva beneath the superior rectus muscle to allow inferior rotation of the globe and exposure of the encapsulated bleb for a prior-placed glaucoma drainage device. (Still 2.jpeg)

Step 3: A conjunctival incision is made through the tenons capsule to the base of the encapsulated bleb. (Still 3. jpeg)

Step 4: Viscoelastic is injected intracamerally to produce positive pressure of aqueous into the bleb, and to prevent transient hypotony upon opening of the encapsulated bleb. (Still 4.jpeg)

Step 5: A sharp blade (stainless steel or diamond) is positioned to incise the encapsulated bleb just above the plane of the existing implant reservoir rim. (Still 5.jpeg)

Step 6: The blade is passed into the bleb and used to ensure the opening is of an appropriate size to allow snug passage of the implant without leakage. (Still 6.jpeg)

Step 7: The anterior margin of the implant is introduced into the encapsulated bleb reservoir space through the conjunctiva, tenons, and fibrotic bleb wall. (Still 7.jpeg)

Step 8. A stiff intra-tube blunt trochar instrument is used to help seat the stop element within the internal wall of the encapsulated bleb. (Still 8jpeg)

Step 9: The anterior component of the shunt is securely within the bleb, stable without sutures. At this stage additional viscoelastic can be injected into the anterior chamber to ensure that there is free flow through the old and new shunt systems. (Still 9.jpeg)

Step 10: The Posterior tube is grasped and flexed, poised for insertion into the retrobulbar space through the same tenoconjunctival entry site. (Still 10.jpeg)

Step 11: The tube is inserted into the posterior aspect of the incision. The retrobulbar space approach can be opened with blunt dissection using a muscle hook or other instrument, as shown at the lower left of the photograph. (Still 11.jpeg)

Step 12: The tube is readily introduced into the retrobulbar space with elevation of the tenoconjunctiva. (Still 12 jpeg)

Step 13: With the tube visibly in proper position, the grommet sutures may be placed to secure the implant again to the external bleb wall or sclera. (Still 12.5 jpeg)

Step 14: Sutures are placed through the various grommet holes and tied in place. (Still 13jpeg & Still 14.jpeg)

Figure 2:
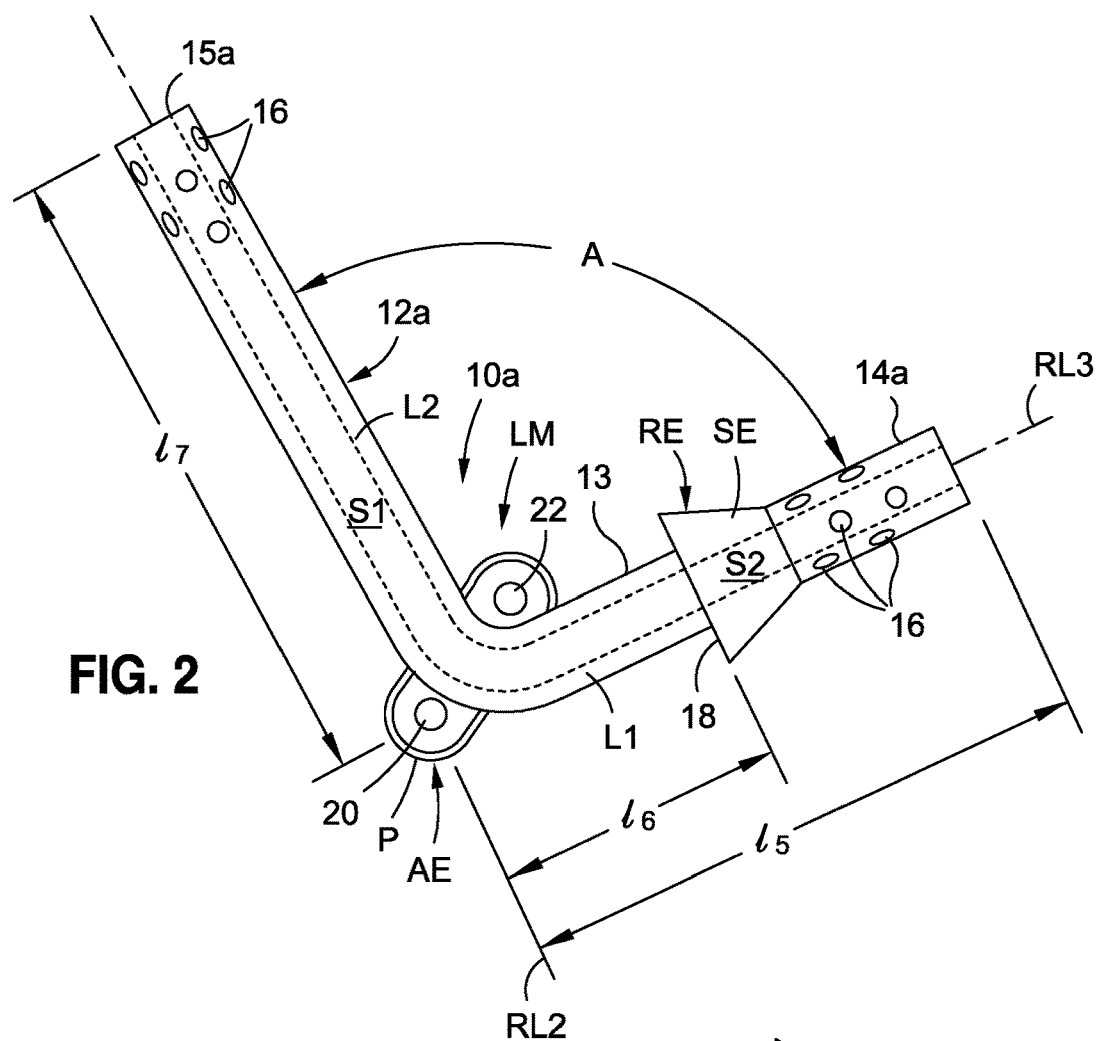
FIG. 2 is plan view of another embodiment of our bleb drainage device.
Figure 2A:
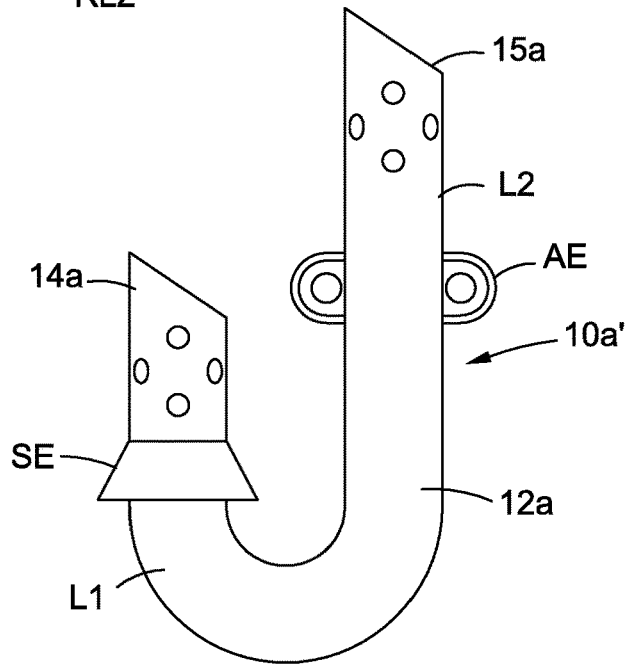
FIG. 2A is plan view of another embodiment of our bleb drainage device similar to that shown in FIG. 2.

Step 15: The conjunctiva is closed with absorbable suture to produce a watertight seal around the implant. (Still 15. jpeg & Still 16 jpeg)) According to another embodiment of our method, the device 10a depicted in FIG. 2 is used and its proximal end 14a is inserted into an anterior portion of a bleb B to relieve pressure. The advantage of this embodiment of our method is that less drastic surgery is called for, because it is easier to access the anterior portion of a bleb B. Furthermore, the surgeon can adjust the location of the tube depending on the condition of the patient's eye.

Ophthalmic Product and Method

Figure 8A:
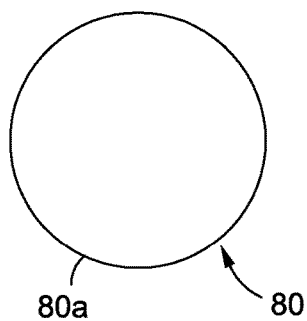
FIGS. 8A through 8C are the components of one embodiment of our ophthalmic product shown in FIG. 9.
Figure 8B:
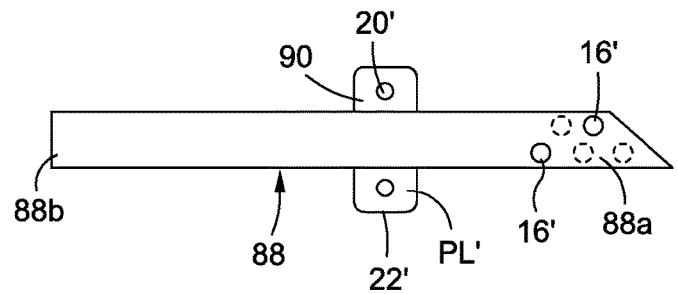
Figure 8C:
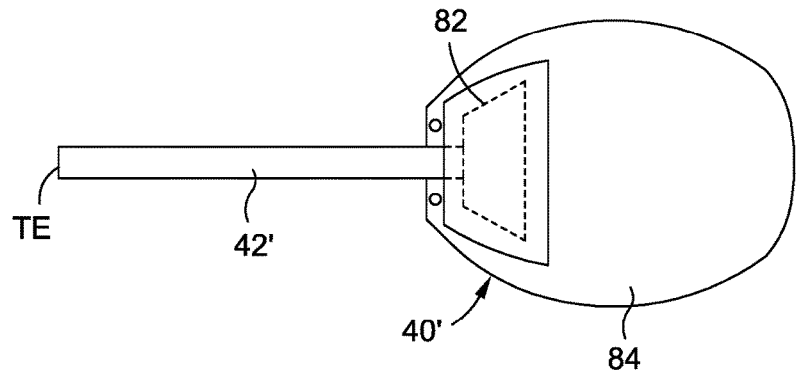
Figure 9:
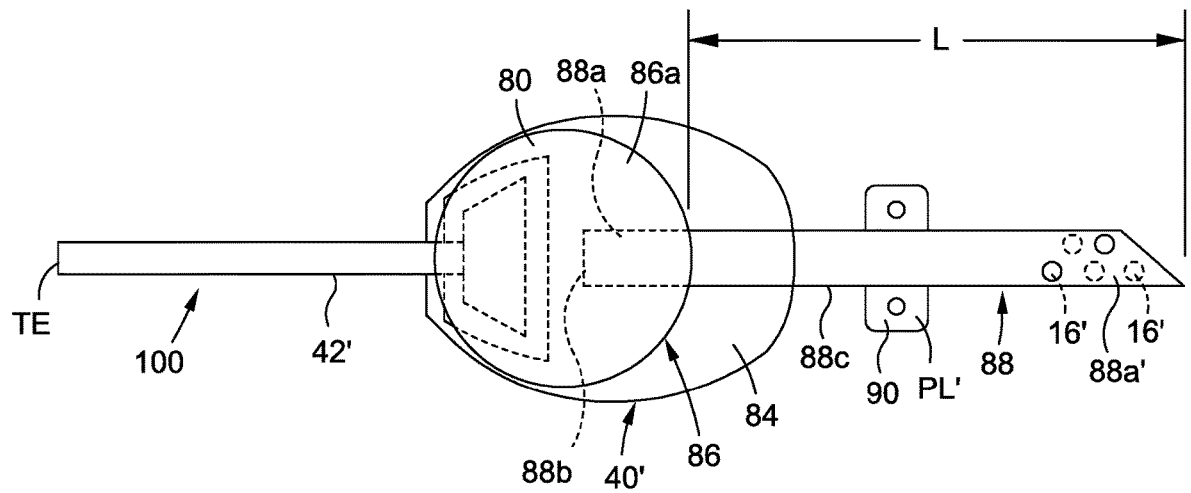
FIG. 9 is a schematic plan view of our ophthalmic product.

As shown in FIGS. 8A through 9, our ophthalmic product 100 comprises a glaucoma drainage device including a tube 42' extending from the glaucoma drainage device. The tube 42' has a terminal end TE adapted to be inserted into an intraocular chamber of a patient's eye. For example, the glaucoma drainage device may be an Ahmed glaucoma valve 40' (FIG. 8C). The Ahmed glaucoma valve 40' includes a self-regulating glaucoma valve element 82 mounted on a plate 84. The Ahmed glaucoma valve 40' is equipped with an artificial bleb made of an elastic, silicone, biocompatible, plastic membrane 80 (FIG. 8A). The membrane 80, which may be transparent or translucent, overlies and covers the valve element 82 and part of the plate 84. The circular edge 80a of the membrane is bonded, for example by an adhesive, to the plate 84 and valve element 82 to form a sealed enclosure 86. Essentially the entire valve element 82 is within the enclosure 86, and it opens and closes in response to intraocular pressure to drain fluid from the patient's intraocular chamber into the enclosure 86.

A tubular member 88 passes through, and is bonded to, a wall 86a of the enclosure 86. As shown in FIG. 9, this tubular member 88 has a first portion 88a within the enclosure 86 terminating at a first terminal end 88b within the enclosure but offset from the valve element 82 to avoid interfering with the valve's operation. It also has a second portion 88c projecting from the enclosure 86 with a second terminal end 88d terminating exterior to the enclosure. There may be openings 16' in the wall of the tubular member 88 that assist in enabling fluid to exit the open end 88d. If the open end 88d becomes blocked by debris, the openings 16' allow fluid to still enter and exit the tubular members. The end 88d may be beveled. The second portion 88c has a predetermined length L so that, upon implantation of the ophthalmic device, the second end is adapted to be placed in or near retrobulbar space of an eye of a patient. The predetermined length L may be substantially from 3 to 45 millimeters. An anchoring element 90 is along the second portion 88c between the end 88d and the plate 84. The anchoring element 90 comprises a plate PL' having spaced apart openings 20' and 22' that straddle the second portion 88c and are opposed to each other. The anchoring element 90 is at or near the end 88d.

In treating glaucoma using our ophthalmic product 100, the tube 42' of the glaucoma drainage device has its terminal end TE inserted into an intraocular chamber of an eye of a patient to drain fluid from the intraocular chamber. The surgeon places the second end 88d of the tubular member 88 in or near retrobulbar space of the eye of the patient and sutures the anchoring element 90 to the eye. The enclosure 86 functions as an artificial bleb to collect fluid draining from the intraocular chamber through the tube 42' into the enclosure. The fluid in the enclosure 86 drains through the tubular member 88 into the retrobulbar space. Affixing the membrane 80 as illustrated, forms a sealed enclosure 86 that only allows fluid exiting the intraocular chamber to be drained through the enclosure 86 into the tubular member 88 and out the end 88d into the retrobulbar space.

Scope of the Invention

The above presents a description of the best mode we contemplate of carrying out our bleb drainage device and method, and of the manner and process of making and using them in such full, clear, concise, and exact terms as to enable a person skilled in the art to make and use. Our bleb drainage device and method are, however, susceptible to modifications and alternate constructions from the illustrative embodiments discussed above which are fully equivalent. Consequently, it is not the intention to limit our bleb drainage device and method to the particular embodiments disclosed. On the contrary, our intention is to cover all modifications and alternate constructions coming within the spirit and scope of our bleb drainage device and method as generally expressed by the following claims, which particularly point out and distinctly claim the subject matter of our invention.

The invention claimed is:

1. A method of treating glaucoma in an eye of a patient including the step of
   inserting into the patient's retrobulbar space to drain fluid from an intraocular chamber of the patient's eye a terminal open beveled end of a flexible tubular member with a circular cross-section that forms a passageway in the tubular member terminating in said beveled open end,
   said passageway defined at least in part by a wall of the flexible tubular member terminating in said open end, said wall including a plurality of openings at said open end,
   said plurality of openings configured and positioned so that, when said open end and plurality of openings are within the retrobulbar space, the fluid exits through said openings and open end and drains into the retrobulbar space.

2. A method of treating glaucoma in an eye of a patient including the step of
   inserting into the patient's retrobulbar space to drain fluid from an intraocular chamber of the patient's eye a terminal open beveled end of a flexible tubular member with a circular cross-section that forms a passageway in the tubular member terminating in said beveled open end, said flexible tubular member adapted to be bent upon insertion, said passageway defined at least in part by a wall of the flexible tubular member terminating in said open end, said wall including a plurality of openings at said open end, said plurality of openings configured and positioned therein orthogonal to the inserted end of the tubular member, the fluid exiting through said openings and open end to drain into the retrobulbar space, said flexible tubular member having a length from 5 to 60 millimeters and an outside diameter from 0.2 to 3 millimeters, and at least one anchoring element on an exterior of the flexible tubular member that enables said tubular member to be sutured in position.

3. A method of treating glaucoma in an eye of a patient including the steps of mounting to the surface of the globe of the patient's eye a flexible tubular member having an exterior circular wall enclosing a passageway for aqueous fluid from an intraocular chamber of the patient's eye that terminates in an open beveled end including a plurality of openings at said open end, configuring and positioning the flexible tubular member on said surface so that, when said open end and plurality of openings are within the retrobulbar space, the aqueous fluid exits through said openings and open end and drains into the retrobulbar space, and suturing said tubular member to the surface of the globe of the patient's eye in position after inserting into the patient's retrobulbar space the open beveled end so that said open end and said plurality of openings are beyond the surface of the globe to drain directly fluid from the patient's eye into the hydrophobic periorbital fat within the patient's retrobulbar space, a watertight seal forming around the inserted open beveled end, said open beveled end being adapted to be placed in retrobulbar space, and said flexible tubular member being adapted to be bent upon insertion.

\* \* \* \* \*